US006365802B2

(12) United States Patent
Kridl (10) Patent No.: US 6,365,802 B2
(45) Date of Patent: *Apr. 2, 2002

(54) METHODS FOR INCREASING STEARATE CONTENT IN SOYBEAN OIL

(75) Inventor: Jean C. Kridl, Davis, CA (US)

(73) Assignee: Calgene LLC, Davis, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/134,262

(22) Filed: Aug. 14, 1998

(51) Int. Cl.$^7$ .................................................. A01H 5/10
(52) U.S. Cl. ...................................................... 800/312
(58) Field of Search ......................................... 800/312

(56) References Cited

U.S. PATENT DOCUMENTS

| 5,534,425 A | 7/1996 | Fehr et al. |
| 5,557,037 A | 9/1996 | Fehr et al. |
| 5,663,485 A | 9/1997 | Fehr et al. |
| 5,714,668 A | 2/1998 | Fehr et al. |
| 5,760,206 A | 6/1998 | Hitz et al. |
| 5,763,745 A | 6/1998 | Fehr et al. |

FOREIGN PATENT DOCUMENTS

| WO | WO 91/18985 | 12/1991 |
| WO | WO 92/11373 | 7/1992 |
| WO | WO 96/36719 | 11/1996 |
| WO | WO 97/12047 | 4/1997 |
| WO | WO 97/40698 | 11/1997 |

OTHER PUBLICATIONS

Graef GL, et al. "Fatty acid development in a soybean Glycine max mutant with high stearic acid." J. Am. Oil Chem. Soc. 62:773–775 (Abstract only; Biosis Abstract 1985:330136).*

Bachy, R. N. et al., "Accumulation and Assembly of Soybean Beta–Conglycinin in Seeds of Transformed Petunia Plants" *Embo Journal* 4:3047–3053.

List, et al., "Potential Margarine Oils from Genetically Modified Soybeans" *Journal of the American Oil Chemists' Society* 73(6), pp: 729–732, (1996).

Hawkins, et al., "Characterization of Acyl–ACP Thioesterases of Mangosteen *Garcinia mangostana*) Seed and High Levels of Stearate Production in Transgenic Canola" *The Plant Journal* 13(6), pp: 743–752, (1998).

Broun, et al., "A Bifunctional Oleate 12–hydroxylase: Desaturase from *Lesquerella fendleri*" *The Plant Journal* 13(2), pp: 201–210, (1998).

Slocombe, et al., "Temporal and Tissue–Specific Regulation of a *Brassica napus* Stearoyl–Acyl Carrier Protein Desaturase Gene" *Plant Physiology* 104, pp: 1167–1176, (1994).

Knutzon, et al., "Modification of Brassica Seed Oil by Antisense Expression of a Stearoyl–Acyl Carrier Protein Desaturase Gene" *Proceedings of the National Academy of Sciences of the USA* 89, pp: 2624–2628, (1992).

Hartmann, et al., "Association of Elevated Stearate with Agronomic and Seed Traits of Soybean" *Crop Science* 37(1), pp: 124–127, (1997).

Lundeen, et al., "Association of Alleles for High Stearic Acid with Agronomic Characters of Soybean" *Crop Science* 27, pp: 1102–1105, (1987).

Merlo, et al., "Ribozymes Targeted to Stearoyl–ACP Δ9 Desaturase mRNA Produce Heritable Increases of Stearic Acid in Transgenic Maize Leaves" *The Plant Cell* 10, pp: 1603–1621, (1998).

Cummins, et al., "Differential, Temporal and Spatial Expression of Genes Involved in Storage Oil and Oleosin Accumulation in developing Rapeseed Embryos: Implications for the Role of Oleosins and the Mechanisms of Oil–body Formation" *Plant Molecular Biology* 23, pp: 1015–1027, (1993).

Griffiths, et al., "The Regulation of Triacylglycerol Biosynthesis in Cocoa (*Theobroma cacao*) L." *Planta* 184, pp: 279–284, (1991).

Jordan, et al., "Fatty Acid Elongation by a Particulate Fraction from Germinating Pea" *Biochemical Journal* 191, pp: 791–797, (1980).

Hammond, et al., "Registration of A5 Germplasm Line of Soybean (Reg. No. GP44)" *Crop Science* 23, p: 192, (1983).

* cited by examiner

Primary Examiner—Amy J. Nelson
(74) Attorney, Agent, or Firm—Brian K. Stierwalt; Arnold & Porter (57) ABSTRACT

This invention relates to a method for increasing stearate as a component of total triglycerides found in soybean seed. The method generally comprises growing a soybean plant having integrated into its genome a DNA construct comprising, in the 5' to 3' direction of transcription, a promoter functional in a soybean plant seed cell, a DNA sequence encoding an acyl-ACP thioesterase protein having substantial activity on C18:0 acyl-ACP substrates, and a transcription termination region functional in a plant cell. The present invention also provides a soybean seed with about 33 weight percent or greater stearate as a component of total fatty acids found in seed triglycerides.

18 Claims, 6 Drawing Sheets

```
CCAAG ATG TTG AAG CTC TCT TCT TCC CGA AGC CCA TTG GCC CGC ATT CCC      50
      Met Leu Lys Leu Ser Ser Ser Arg Ser Pro Leu Ala Arg Ile Pro
        1               5                  10                  15

ACC CGG CCC AGG CCC AAC TCC ATT CCT CCC CGG ATA ATT GTG GTT TCC        98
Thr Arg Pro Arg Pro Asn Ser Ile Pro Pro Arg Ile Ile Val Val Ser
                 20                  25                  30

TCC TCA TCC AGC AAG GTT AAT CCA CTC AAA ACA GAG GCG GTG GTT TCT       146
Ser Ser Ser Ser Lys Val Asn Pro Leu Lys Thr Glu Ala Val Val Ser
         35                  40                  45

TCG GGG CTG GCT GAC CGG CTC CGG AGC TTG ACC GAG GAC GGG               194
Ser Gly Leu Ala Asp Arg Leu Arg Ser Leu Thr Glu Asp Gly
     50                  55                  60

CTT TCG TAT AAG GAG AAG TTC ATA GTG AGA TGC TAT GAG GTT GGG ATT       242
Leu Ser Tyr Lys Glu Lys Phe Ile Val Arg Cys Tyr Glu Val Gly Ile
             65                  70                  75

AAC AAG ACC GCT ACT GTT GAG ACT ATT GCC AAC CTC TTG CAG GAG GTT       290
Asn Lys Thr Ala Thr Val Glu Thr Ile Ala Asn Leu Leu Gln Glu Val
         80                  85                  90                  95
```

FIGURE 3A

| | | | | | | | | | | | |
|---|---|---|---|---|---|---|---|---|---|---|---|
| GGA | TGC | AAT | CAC | GCC | CAA | AGC | GTT | GGA | TAT | TCG | ACG | GGT | GGG | TTT | TCG |
| Gly | Cys | Asn | His | Ala | Gln | Ser | Val | Gly | Tyr | Ser | Thr | Gly | Gly | Phe | Ser |
|  | 100 |  |  |  |  |  |  |  | 105 |  |  |  |  | 110 | 338 |

```
GGA TGC AAT CAC GCC CAA AGC GTT GGA TAT TCG ACG GGT GGG TTT TCG    338
Gly Cys Asn His Ala Gln Ser Val Gly Tyr Ser Thr Gly Gly Phe Ser
        100                         105                 110

ACA ACC CCT ACC ATG AGA AAA TTG CGT CTG ATA TGG GTT ACT GCT CGC    386
Thr Thr Pro Thr Met Arg Lys Leu Arg Leu Ile Trp Val Thr Ala Arg
        115                         120                 125

ATG CAC ATC GAA ATC TAC AAA TAT CCA GCT TGG AGT GAT GTG GTG GAA    434
Met His Ile Glu Ile Tyr Lys Tyr Pro Ala Trp Ser Asp Val Val Glu
        130                         135                 140

ATA GAG TCG TGG GGC CAG GGT GAA AAA ATC GGA ACC AGA CGT GAT        482
Ile Glu Ser Trp Gly Gln Gly Glu Lys Ile Gly Thr Arg Arg Asp
        145                         150                 155

TGG ATT CTG AGA GAC TAT GCC ACT GGT CAA GTT CAA ATT GGC CGA GCT ACT 530
Trp Ile Leu Arg Asp Tyr Ala Thr Gly Gln Val Gln Ile Gly Arg Ala Thr
        160                         165                 170             175

AGC AAG TGG GTA ATG ATG AAC CAA GAC CGA CTT CAA AAA GTC            578
Ser Lys Trp Val Met Met Asn Gln Asp Arg Leu Gln Lys Val
        180                         185                 190

GAT GTT CGT GAT GAG TAC TTG GTT CAC TGT CCA AGA GAA CTC            626
Asp Val Arg Asp Glu Tyr Leu Val His Cys Pro Arg Glu Leu
        195                         200                 205
```

FIGURE 3B

```
AGA TTG GCA TTT CCA GAG GAA AAT AGC AGC TTG AAG AAA ATT TCA        674
Arg Leu Ala Phe Pro Glu Glu Asn Ser Ser Leu Lys Lys Ile Ser
                210                 215                 220

AAA CTT GAA GAT CCT TCT CAA TAT TCG AAG CTG GGG CTT GTG CCT AGA    722
Lys Leu Glu Asp Pro Ser Gln Tyr Ser Lys Leu Gly Leu Val Pro Arg
        225                 230                 235

AGA GCA GAT CTG GAC ATG AAT CAA CAT GTT AAT AAT GTC ACC TAT ATT    770
Arg Ala Asp Leu Asp Met Asn Gln His Val Asn Asn Val Thr Tyr Ile
            240                 245                 250        255

GGA TGG GTG GAG AGC ATG CCT CAA GAA ATC ATT GAT ACC CAT GAA        818
Gly Trp Val Glu Ser Met Pro Gln Glu Ile Ile Asp Thr His Glu
                260                 265                 270

CTG CAA ACC ATA ACA TTA GAC TAC AGA CGG GAA TGC CAA CAT GAT GAT    866
Leu Gln Thr Ile Thr Leu Asp Tyr Arg Arg Glu Cys Gln His Asp Asp
        275                 280                 285

GTG GTT GAT TCC TTG ACT AGT CCA GAG CCT TCT GAA GAT GCT GAA GCA    914
Val Val Asp Ser Leu Thr Ser Pro Glu Pro Ser Glu Asp Ala Glu Ala
            290                 295                 300

GTT TTC AAC CAT AAT GGA ACA AAT GGG TCT GCA AAT GTG AGC GCC AAC    962
Val Phe Asn His Asn Gly Thr Asn Gly Ser Ala Asn Val Ser Ala Asn
        305                 310                 315
```

FIGURE 3C

```
GAC CAT GGA TGC CGC AAC TTT CTG CAT CTA CTA AGA TTG TCG GGC AAT    1010
Asp His Gly Cys Arg Asn Phe Leu His Leu Leu Arg Leu Ser Gly Asn
320                 325                 330                 335

GGA CTT GAA ATC AAC CGT GGT CGT ACT GAG TGG AGA AAG AAA CCT ACA    1058
Gly Leu Glu Ile Asn Arg Gly Arg Thr Glu Trp Arg Lys Lys Pro Thr
            340                 345                 350

AGA TGAGGCAATA AAGTACATTA TGTACTTTAT CGTTGCTTTA GCCGGCTTCT         1111
Arg

GGATGGTGAT TTCTTTCTGC ATTCCTTCTT TCCTTTTTGT TTTCCTAGGG TATCCTTCGC  1171

TTCTTGCCTG TAAGAGTATT ATGTTTTCCG TTTGCCCTGA AGTTGTAAAT TTGTCGAGGA  1231

ACTCGAGTCA TTGTTTGAAT CGAGGATGGT GAGAAGTGTA CTTGTTTGTT GTATTCCATT  1291

CTTCCTGAT                                                         1300
```

FIGURE 3D

METHODS FOR INCREASING STEARATE CONTENT IN SOYBEAN OIL

FIELD OF THE INVENTION

The invention relates to genetic modification of plants, plant cells and seeds, particularly altering fatty acid composition.

BACKGROUND

Soybean (*Glycine max*) is one of the highest value crops currently grown in the United States (≈$16 billion in 1996). Ranking close to corn (25%) and wheat (22%), soybean accounted for 19% of the United States crop acres planted in 1994. Often referred to as a "miracle crop", soybean offers tremendous value through the oil, protein and whole soybean products. Agronomic traits, food quality traits related to oils and protein quality are all important for the soybean industry.

More soybeans are grown in the United States than anywhere else in the world (2.4 billion bushels in 1996, 50% of world production). A bushel of soybean (60 pounds) is comprised of 48 pounds of protein meal and 11 pounds of oil. While protein meal is the major component in soybean, oil, lecithin, tocopherols, isoflavones, etc. are all co-products and add value to the bean. Soybean oil is the major edible oil used in the world (40% of the 59.4 million metric tons in 1993). It also accounts for 70% of the 14 billion pounds of edible vegetable oil in the United States. The primary food applications where the oil is used extensively are for baking and frying (40–45%), salad and cooking oil (40–45%), margarine and shortening (15–20%) and a wide spectrum of processed foods. Development of other vegetable oils for specialty uses has recently affected the acreage and production of soybean. The low cost and ready availability of soybean oil provide an excellent opportunity to upgrade this commodity item for specialty uses.

Food fats and oils are chemically composed of triesters of glycerol containing straight chain, normal aliphatic fatty acids, also referred to herein as triacylglycerols or triglycerides (TAG). The properties of food fats and oils are a reflection of the fatty acids contained in the TAG and their distribution on the glycerol backbone. When the melting point of the TAG is below room temperature, the TAG is referred to as an "oil". Triglycerides that melt above room temperature are referred to as "fat". Gradients between fluidity and solidity exist. Partially solidified, non-pourable triglycerides are often referred to as "plastic fats".

Fatty acids are organic acids having a hydrocarbon chain ranging in length from about 4 to 24 carbons. Fatty acids differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds.

Typically, oil derived from commercial soybean varieties is composed of approximately 11% palmitic (C16:0), 4% stearic acid (C18:0), 21% oleic acid (C18:1), 56% linoleic acid (C18:2), and 10% linolenic acid (C18:3). The fatty acid composition of soybean oil, as well as all oils, largely determines its physical and chemical properties, and thus its uses.

Fatty acid biosynthesis has been the subject of research efforts in a number of organisms. For reviews of fatty acid biosynthesis in plants, see Ohlrogge et al., (1995) *Plant Cell*, 7:957–970, Ohlrogge et al., (1997) *Annu Rev Plant Physiol Plant Mol Biol*, 48:109–136 and Sommerville et al. (1991) *Science*, 252:80–87.

As mentioned previously, the fatty acid composition of an oil determines its physical and chemical properties, and thus its uses. Plants, especially plant species which synthesize large amounts of oils in plant seeds, for example soybean, are can important source of oils both for edible and industrial uses. Various combinations of fatty acids in the different positions in the triglyceride will alter the properties of the triglyceride. For example, if the fatty acyl groups are mostly saturated fatty acids, then the triglyceride will be solid at room temperature. In general, however, vegetable oils tend to be mixtures of different triglycerides. The triglyceride oil properties are therefore a result of the combination of triglycerides which make up the oil, which are in turn influenced by their respective fatty acid compositions.

Plant breeders have successfully modified the yield and fatty acid composition of various plant seed oils by introducing desired traits through plant crosses and selection of progeny carrying the desired trait forward. Application of this technique thus is limited to traits which are found within the same plant species. Alternatively, exposure to mutagenic agents can also introduce traits which may produce changes in the composition of a plant seed oil. However, it is important to note that Fatty Acid Synthesis (FAS) occurs in most tissues of the plant including leaf (chloroplasts) and seed tissue (proplastids). Thus, although a mutagenesis approach can sometimes result in a desired modification of the composition of a plant seed oil, it is difficult to effect a change which will not alter FAS in other tissues of the plant.

A wide range of novel vegetable oils compositions and/or improved means to obtain or manipulate fatty acid compositions, from biosynthetic or natural plant sources, are needed. Plant breeding, even with mutagenesis, cannot sufficiently meet this need and provide for the introduction of novel oil.

For example, cocoa-butter has certain desirable qualities (mouthfeel, sharp melting point, etc.) which are a function of its triglyceride composition. Cocoa-butter contains approximately 24.4% palmitate (16:0), 34.5% stearate (18:0), 39.1% oleate (18:1) and 2% linoleate (18:2). Thus, in cocoa butter, palmitate-oleate-stearate (POS) comprises almost 46% of triglyceride composition, with stearate-oleate-stearate (SOS) and palmitate-oleate-palmitate (POP) comprising the major portion of the balance at 33% and 16%, respectively, of the triglyceride composition. Other novel oils compositions of interest might include trierucin (three erucic) or a triglyceride with medium chain fatty acids in each position of the triglyceride molecule.

Plant seed oils contain fatty acids acylated at the sn-1, sn-2, and sn-3 positions of a glycerol backbone, referred to as a triacylglycerol (TAG). The structure of the TAG, as far as positional specificity of fatty acids, is determined by the specificity of enzymes involved in acylating the fatty acyl CoA substrates to the glycerol backbone. For example, there is a tendency for such enzymes from many temperate and tropical crop species to allow either a saturated or an unsaturated fatty acid at the sn-1 or the sn-3 position, but only an unsaturated fatty acid at the sn-2 in the seed TAGs. In some species such as cocoa, TAG compositions suggest that this tendency is carried further in that there is an apparent preference for acylation of the sn-3 position with a saturated fatty acid, if the sn-1 position is esterified to a saturated fatty acid. Thus, there is a higher percentage of structured TAG of the form Sat-Un-Sat (where Sat= saturated fatty acid and Un=unsaturated fatty acid).

Of particular interest are triglyceride molecules in which stearate is esterified at the sn-1 and sn-3 positions of a triglyceride molecule with unsaturates in the sn-2 position particularly oleate. Vegetable oils rich in such SOS (Stearate-Oleate-Stearate) molecules share certain desirable qualities with cocoa butter yet have a degree of additional hardness when blended with other structured lipids. SOS—containing vegetable oils are currently extracted from relatively expensive oilseeds from certain trees grown in tropical areas such as Sal, Shea, and Illipe trees from India, Africa, and Indonesia respectively. Cheaper and more conveniently grown sources for SOS-type vegetable oils are desirable.

In addition, vegetable oils rich in stearate fatty acid content tend to be solid at room temperature. Such vegetable fats can be used directly in shortenings, margarine and other food "spread" products, obviating the need for chemical hydrogenation. Hydrogenation is a process whereby molecular hydrogen is reacted with the unsaturated fatty acid triglyceride until the desired degree of solidity is obtained. The solidity is commonly determined by the solid fat index (SFI, Official and Tentative Methods, American Oil Chemists' Society, Cd 10-57(93), Champaign, Ill.). Values are determined by dilatometry (expansion in volume) over a defined temperature range of 50°, 70° 80°, 92° and 100° or 104° F. The hydrogenation process converts unsaturated fatty acids to partially or fully saturated fatty acids, and increases the heat and oxidative stability of the product. The iodine value (IV) measures the degree of unsaturation of a fat. Lower values indicate greater saturation. The oxidative stability may be measured by an oil stability index (Official and Tentative Methods, American Oil Chemists' Society, Cd 1b-87,Champaign, Ill.) and active oxygen method (AOM, Official and Tentative Methods, American Oil Chemists' Society, Cd 12h-92, Champaign, Ill.). The cost and any other factors associated with chemical hydrogenation, such as the production of trans fatty acids, can be avoided if the vegetable oil is engineered to be stearate rich in the plant seed.

Moreover, some plant tissues use 18 carbon fatty acids as precursors to make other compounds. These include saturated long chain fatty acids longer than 18 carbons in length. Since very little stearate typically accumulates in soybean plants, it may be necessary to increase stearate accumulation if one wants to increase production of compounds which depend upon supply of stearate fatty acids for synthesis.

The fatty acid composition of soybean oil described above is often considered less than optimal in terms of oil functionality. While the limitations of the fatty acid composition may be partly overcome by chemical hydrogenation, the trans fatty acids produced as a result of the hydrogenation process are Sat-Un-Satpected of having unfavorable health effects (Mensink, et al. (1990) *N. Eng. J. Med.* 323:439–445).

Through the efforts of traditional plant breeding techniques, the fatty acid composition of soybeans has been improved. For example, using mutagenesis, plant breeders have been able to increase the amount of stearate (C18:0) produced in the soybean oil. In such high stearate lines, designated as A6 (ATCC Accession No. 97392, Hammond and Fehr, (1983) *Crop Science* 23:192), stearate levels of up to about 25 weight percent of the total fatty acid composition have been achieved. Such high stearate containing lines have been further bred with mutant soybean lines containing elevated levels of palmitate (16:0). Soybean lines containing the elevated stearate levels produced by mutagenesis demonstrate a negative correlation of increased stearate content and seed yield (Hartmann, et al. (1997) *Crop Science* 37:124–127). Attempts to further increase the stearate content and/or improve the seed yield of such increased stearate lines by breeding have thusfar proven unsuccessful.

List, et al. ((1996) *J. Am. Oil. Chem. Soc.* 73:729–732) describes the use of genetically modified soybean oils in margarine formulations. High stearate oil from soybean variety A6 was found to have an insufficient solid fat index at 24.7° C. and higher temperatures to make margarine. The soybean oil was blended with cottonseed or soybean hardstocks to afford mixtures with sufficient solids content for formulation into margarine.

While soybean based products are a major food source, improvements to the nutritional and commercial quality of this product could add further value to soybean based products. Alteration of the soybean oil content and composition could result in products of higher nutritional content and greater stability. The need for industrial hydrogenation of polyunsaturated oil for food applications could be reduced by the preparation of soybean oil with increased concentrations of stearate.

Literature

Hammond and Fehr, (1983) *Crop Science* 23:192 provides the registration of the A6 soybean line with elevated stearate levels. Lundeen, et al. (1987) *Crop Science* 27:1102–1105 and Hartmann, et al. (1997) *Crop Science* 37:124–127 describe the negative association of seed yield with the elevated stearate levels produced using the fasa allele. Fehr and Hammond, U.S. Pat. No. 5,714,668 provides a soybean with an elevated level of stearic acid ranging between 20% and 32% with a low level of liolenic acid (less than 3.0%). Fehr and Hammond, U.S. Pat. No. 5,557,037 provides a soybean plant capable of producing an oil with a palmitic acid content of about 14% to about 24% and a stearic acid content of from about 20% to about 30%.

SUMMARY OF THE INVENTION

The present invention is directed to methods for producing soybean oil having high levels of stearate (C18:0). The method of producing a soybean oil containing increased levels of stearate comprises expression of an acyl-ACP thioesterase capable of producing C18:0 in the seed tissue of the soybean. In particular, the acyl-ACP thioesterase has substantial activity toward 18:0 acyl-ACP substrates, and preferably has little or no activity towards 16:0 acyl-ACP substrates.

The method generally comprises growing a soybean plant containing a construct comprising as operably linked components in the 5' to 3' direction of transcription, a transcription initiation region functional in a seed tissue and a DNA encoding an acyl-ACP thioesterase with substantial activity towards 18:0 acyl-ACP substrates and a transcription termination sequence.

The stearate content of the soybean oil preferably comprises greater than 20%, more preferably greater than about 33% of the fatty acid moieties in the oil. The oil of the present invention may be used as a blending source to make a blended oil product, or it may also be used in the preparation of food.

In another embodiment of the present invention, a soybean oil having an increased saturated fatty acid composition is provided. Soybean oils with saturated fatty acid compositions of greater than 50 weight percent are exemplified herein.

In yet another embodiment of the instant invention, the novel soybean oil, comprising the increased total saturated fatty acid compositions, provides a novel source of structured TAG of the Sat-Un-Sat (saturated-unsaturated-saturated) form.

The novel soybean oil as well as the soybean seed containing the novel oil finds use in many applications.

DETAILED DESCRIPTION OF THE INVENTION

In accordance with the subject invention, constructs and methods are provided for the production of soybean plants with an increased level of stearate (C18:0), as a percentage of the total fatty acids, in the seed oil. The methods for producing such soybean plants comprise transforming a soybean plant with expression constructs comprising a promoter sequence functional in a plant seed operably linked to a DNA sequence encoding a plant acyl-ACP thioesterase having substantial activity toward 18:0-ACP substrates, preferably those with little or no activity toward 16:0-ACP substrates (hereinafter referred to as stearoyl-ACP thioesterase), and a transcription termination sequence. The expression constructs provide an increase in the levels of stearate fatty acids in the seed oil of the transformed soybean plants.

As described in more detail in the examples that follow, an acyl-ACP thioesterase coding sequence from mangosteen (*Garcinia mangostana*), Garm FatA1 (Hawkins and Kridl (1998) *Plant Journal* 13(6):743–752; and PCT Patent Application WO 96/36719, the entireties of which are incorporated herein by reference) is used in expression constructs to generate transgenic soybean plants with increased production of the stearoyl-ACP thioesterase in host cells. In particular the constructs are used to direct the expression of the Garm FatA1 thioesterase in plant seed cells for modification of triacylglycerol (TAG) fatty acid composition to provide increased levels of C18:0 fatty acyl groups. Furthermore, the constructs of the present invention may find use in plant genetic engineering applications in conjunction with plants containing elevated levels of C18:0 (stearate) fatty acids. Such plants may be obtained by antisense gene regulation of stearoyl-ACP desaturase using methods described by Knutzon et al. (*Proc. Nat. Acad. Sci.* (1992) 89:2624–2628), and may also be obtained by co-suppression using sense expression constructs of the stearoyl-ACP desaturase gene, or by conventional mutation and plant breeding programs. In addition, the constructs and methods for increasing stearate in soybean seed may also find use in plant genetic engineering applications in conjunction with plants containing elevated levels of oleate (C18:1) and/or decreased levels of linoleate (C18:2) fatty acids and/or linolenate (18:3). Such plants with elevated levels of oleate and/or with decreased levels of linoleate and/or linolenate may be obtained through genetic engineering, or by conventional mutation and plant breeding programs.

A plant acyl-ACP thioesterase DNA sequence useful for the preparation of expression constructs for the alteration of stearate levels as described herein encodes for amino acids, in the form of a protein, polypeptide or peptide fragment, which amino acids demonstrate substantial activity on 18:0 acyl-ACP substrates and little or no activity on 16:0-ACP to form 18:0 free fatty acid (i.e., stearate) under plant enzyme reactive conditions. By "enzyme reactive conditions" is meant that any necessary conditions are available in an environment (i.e., such factors as temperature, pH, lack of inhibiting substances) which will permit the enzyme to function.

DNA sequences encoding for acyl-ACP thioesterase enzymes with substantial activity on 18:0 acyl-ACP substrates and little or no activity on 16:0-ACP to form 18:0 free fatty acid (i.e., stearate) are known in the art and are described in Hawkins and Kridl (1998) supra, and PCT Patent Application WO 96/36719. The Garm FatA1 DNA sequence described therein and used herein demonstrates preferential activity on C18:1 acyl-ACP substrate, and also demonstrates substantial activity (approximately 25% of the 18:1 activity) on C18:0 acyl-ACP substrates. Only a small increase in C16:0 activity over activity in control cells is observed, and the 16:0 activity represents only approximately 3% of the 18:1 activity.

In preparing the expression constructs, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

For the most part, the constructs will involve regulatory regions functional in plants which provide for modified production of plant stearoyl-ACP thioesterase, and modification of the fatty acid composition. The open reading frame, coding for the plant stearoyl-ACP thioesterase or functional fragment thereof will be joined at its 5' end to a transcription initiation regulatory region such as the wild-type sequence naturally found 5' upstream to the thioesterase structural gene, or to a heterologous regulatory region from a gene naturally expressed in plant tissues. Examples of useful plant regulatory gene regions include those from T-DNA genes, such as nopaline or octopine synthase, plant virus genes, such as CaMV 35S, or from native plant genes.

For such applications when 5' upstream non-coding regions are obtained from other genes regulated during seed maturation, those preferentially expressed in plant embryo tissue, such as ACP, napin and β-conglycinin 7S subunit transcription initiation control regions, as well as the Lesquerella hydroxylase promoter (described in Broun, et al. (1998) *Plant Journal* 13(2):201–210 and in U.S. patent application Ser. No. 08/898,038) and the stearoyl-ACP desaturase promoter (Slocombe, et al. (1994) *Plant Physiol.* 104:1167–1176), are desired. Such "seed-specific promoters" may be obtained and used in accordance with the teachings of U.S. Pat. No. 5,420,034 having a title "Seed-Specific Transcriptional Regulation" and in Chen et al., (1986), *Proc. Natl. Acad. Sci.*, 83:8560–8564. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant stearoyl-ACP thioesterase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention. As described herein, transcription termination sequences derived from DNA sequences preferentially expressed in plant seed cells are employed in the expression constructs of the present invention.

The method of transformation is not critical to the instant invention; various methods of plant transformation are currently available. As newer methods are available to transform crops, they may be directly applied hereunder. For example, many plant species naturally Sat-Un-Satceptible to Agrobacterium infection may be successfully transformed via tripartite or binary vector methods of Agrobacterium-mediated transformation. In addition, techniques of microinjection, DNA particle bombardment, and electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species in which the expression construct or components thereof are introduced, one or more markers may be employed, where different conditions for selection are used for the different hosts. A number of markers have been developed for use for selection of transformed plant cells, such as those which provide resistance to various antibiotics, herbicides, or the like. The particular marker employed is not essential to this invention, one or another marker being preferred depending on the particular host and the manner of construction.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Various methods of transforming cells of soybean have been previously described. Examples of soybean transformation methods have been described, for example, by Christou et al. U.S. Pat. No. 5,015,580 and by Hinchee et al. U.S. Pat. No. 5,416,011, the entireties of which are incorporated herein by reference.

Once a transgenic plant is obtained which is capable of producing seed having a modified fatty acid composition, traditional plant breeding techniques, including methods of mutagenesis, may be employed to further manipulate the fatty acid composition. Alternatively, additional foreign fatty acid modifying DNA sequence may be introduced via genetic engineering to further manipulate the fatty acid composition.

One may choose to provide for the transcription or transcription and translation of one or more other sequences of interest in concert with the expression of a plant stearoyl-ACP thioesterase in a plant host cell. In particular, the reduced expression of stearoyl-ACP desaturase in combination with expression of a plant stearoyl-ACP thioesterase may be preferred in some applications.

When one wishes to provide a plant transformed for the combined effect of more than one nucleic acid sequence of interest, typically a separate nucleic acid construct will be provided for each. The constructs, as described above contain transcriptional or transcriptional and translational regulatory control regions. The constructs may be introduced into the host cells by the same or different methods, including the introduction of such a trait by the inclusion of two transcription cassettes in a single transformation vector, the simultaneous transformation of two expression constructs, retransformation using plant tissue expressing one construct with an expression construct for the second gene, or by crossing transgenic plants via traditional plant breeding methods, so long as the resulting product is a plant having both characteristics integrated into its genome.

By decreasing the amount of stearoyl-ACP desaturase, an increased percentage of saturated fatty acids is provided. Using anti-sense, transwitch, ribozyme or some other stearoyl-ACP desaturase reducing technology, a decrease in the amount of stearoyl-ACP desaturase available to the plant cell is produced, resulting in a higher percentage of saturates such as one or more of stearate (C18:0), arachidate (C20:0), behenate (C22:0) and lignocerate (C24:0). In rapeseed reduced stearoyl-ACP desaturase results in increased stearate levels and total saturates (Knutzon et al. (1992) *Proc. Nat. Acad. Sci* 89:2264–2628).

Of special interest is the production of triglycerides having increased levels of stearate. In addition, the production of a variety of ranges of stearate is desired. Thus, plant cells having lower and higher levels of stearate fatty acids are contemplated. For example, fatty acid compositions, including oils, having a 10% level of stearate as well as compositions designed to have up to an approximate 60% level of stearate or other such modified fatty acid(s) composition are contemplated.

As described in more detail in the examples that follow, constructs are prepared to direct the expression of a stearoyl- ACP thioesterase in plant seed tissue. Such expression constructs allow for the increase in 18:0 levels in oils obtained from the seeds of transformed soybean plants. Increases in the levels of stearate in soybeans transformed to express Garm FatA1 range from 4 fold to approximately 13 fold over the levels obtained in seeds from nontransformed control plants. Additionally, by decreasing the amount of stearoyl-ACP desaturase available to the plant FAS complex in conjunction with an increase of the amount of stearoyl-ACP thioesterase available, a more marked increased percentage of stearate may be obtained. By manipulation of various aspects of the DNA constructs (e.g., choice of promoters, number of copies, etc.) and traditional breeding methods, one skilled in the art may achieve even greater levels of stearate. By expression of a plant stearoyl-ACP thioesterase in seed tissue or a decrease in the expression of stearoyl-ACP desaturase or a combination of both, an increased percentage of stearate can be achieved in soybean. In addition, modified thioesterase encoding DNA sequences may find use for increasing stearate levels in seed tissue. Such modified thioesterase sequences may be obtained as described in PCT Patent Application WO 96/36719.

Surprisingly, in the oil of seeds from T2 soybean lines transformed to express the Garm FatA1 DNA sequence from the β-conglycinin 7S subunit promoter, stearate levels of up to 53 percent as a percentage of the total fatty acid composition are obtained. In addition, in the oil of the initial transformed lines expressing Garm FatA1 DNA sequence from the β-conglycinin 7S subunit promoter increases in the levels of stearate obtained from individual seeds range from about 14 weight percent up to about 53 weight percent. Furthermore, transgenic soybean plants expressing the Garm FatA1 DNA sequence from the napin derived promoter accumulate increased levels of stearate ranging from approximately 20 weight percent up to approximately 45 weight percent in individual seeds of T2 soybean lines. Stearate levels obtained from the oil of individual seeds of nontransformed control soybeans range from approximately 4 weight percent to approximately 6 weight percent. Preferred oil compositions for many applications include 33 weight percent or greater stearate fatty acids as a component of the soybean oil.

In addition, transformed soybean lines containing increased stearate levels of the present invention also demonstrate an increase in the total levels of saturated fatty acids. Transformed soybean lines containing elevated stearate levels also contain increased levels of Arachidic acid (20:0) and Behenic acid (22:0). Increases in 20:0 range from about 3 fold to about 11 fold over the levels of 20:0 obtained from the seed oil of nontransgenic control soybean lines. Increases in 22:0 range from about 2 fold to about 5 fold over the levels of 22:0 obtained from the seed oil of nontransgenic control soybean lines.

Thus, in soybean lines transformed to express a stearoyl-ACP thioesterase in the seed tissue, total saturated fatty acids (16:0, 18:0, 20:0 and 22:0) comprise at least 30 percent of the total fatty acids as a percentage of weight, preferably above 50 weight percent. In some cases, total saturated fatty acid levels of above about 65 weight percent may be obtained.

The novel soybean oil compositions of the present invention comprise increased total saturated fatty acids and provide a novel source of structured TAG of the Sat-Un-Sat form. For oil compositions having greater than about 33 weight percent stearate the Sat-Un-Sat form of TAG may comprise 25 percent or greater of the total TAG composition as a stearate-unsaturated-stearate form of TAG. It is apparent that by utilizing a high oleic acid soybean line that one may produce a soybean oil with a high proportion of a stearate-oleate-stearate form of TAG. An example of such high oleic acid soybean oil is described in PCT Application WO 97/40698.

The soybean oil compositions of the present invention containing novel fatty acid compositions may find use in a number of applications, without the need for chemical modifications prior to use as described herein, or as described in PCT application titled "Food Products Containing Structured Triglycerides", PCT/U.S. Pat. No. 97/06037, the entirety of which is incorporated herein by reference. The soybean oil of the present invention may find use in the preparation of foods to facilitate cooking or heating applications.

The soybean oils produced by the methods of the present invention may be used in the formation of emulsions comprising water and soybean oil. The soybean oil may be treated by interesterification prior to the formation of an emulsion. As used herein, interesterification refers to the process of rearranging the glyceride structure of fats. Interesterification is accomplished by a chemical reaction in which fatty acids are rearranged on the glycerol molecule without modification of the fatty acids themselves. An emulsion may preferably comprise between about 70% and about 90% by volume soybean oil, and between 10% and about 30% by volume water. The aqueous emulsion may further be defined as margarine. As used herein, the term "margarine" refers to an edible emulsion comprising oil and water that is both solid and spreadable at 25° C.

Alternatively, the soybean seeds containing the modified fatty acid compositions of the present invention, may be used to prepare soymilk. Soymilk may be prepared by the steps of selecting soybean seeds, contacting the seeds with water to form a mixture, heating the mixture, grinding the mixture, and removing the solids to form soymilk. Removal of solids may be accomplished by methods including, but not limited to, filtration, sedimentation and centrifugation. The heating step may comprise heating the mixture to any temperature suitable for the formation of tofu, preferably to a temperature sufficient to inactivate the trypsin inhibitor in the liquid at least about 80% as compared to the trypsin inhibitor activity prior to heating, and most preferably to a temperature between about 90° and about 100° C. Trypsin inhibitor activity may be conveniently assayed using calorimetric method described in Liu and Markakis ((1989), *Cereal Chem* 66(5):415–422).

Soybean seeds containing the novel soybean oil compositions of the present invention may find use in the preparation of tofu. Tofu may be prepared by the steps of selecting soybean seeds containing soybean oil having oil compositions of the present invention, contacting the seeds with water to form a mixture, heating the mixture, grinding the mixture, removing the solids to form a filtrate, adding a coagulant, and cooling the filtrate to form tofu. The coagulant used may be, but is not limited to, glucono-δ-lactone, lemon juice, sea salt, calcium sulfate or magnesium chloride. Removal of solids may be accomplished by methods including, but not limited to filtration, sedimentation, and centrifugation. The heating step may comprise heating the mixture to any temperature suitable for the formation of tofu, preferably to a temperature sufficient to inactivate the trypsin inhibitor in the liquid at least about 80% as compared to the trypsin inhibitor activity prior to heating, and most preferably to a temperature between about 90° and about 100° C. Trypsin inhibitor activity may be conveniently assayed using calorimetric method described in Liu and Markakis ((1989), *Cereal Chem* 66(5):415–422). The cooling step may comprise cooling the filtrate to any temperature suitable for the formation of tofu, and more preferably to between about 0° C. and about 25° C.

Soy flour may also be prepared from soybean seeds containing the oil compositions of the present invention. A method for preparation of soy flour comprises the steps of selecting soybean seeds and grinding the seeds to produce soy flour. Preferably, the soybean seeds contain soybean oil having increased levels of stearate. The grinding step may be performed by any means suitable for the production of soy flour, including, but not limited to, grinding with wheels, mortar and pestle, plates and blades.

The soybean oil of the present invention may be further used to prepare shortenings. As used herein, the term "shortening" refers to fats, usually plastic in nature, that provide functional effects related to structure, texture and the eating qualities of a variety of food products. The shortening prepared based on the soybean oil of the present invention may also include the incorporation of emulsifiers or surfactants (selected from 21 C.F.R. 172), such emulsifiers used to provide additional functional effects in the final food product. The shortening based on the soybean oil of the present invention may also include a variety of hardstocks (fully hydrogenated triglycerides sourced from a variety of common food oils) that could be used to modify or augment the SFC of the final product and, hence, the physical properties and functionality of the final blend. The plasticity and crystal structure of the final shortening composition based on the soybean oil of the present invention, whether emulsified or not, may be further modified through the process of controlled crystallization and specific gravity reduction known as votation. In this process, the molten shortening described variously above is fed through a scraped-surface heat exchanger, and crystallized in a directed manner-usually in the most functional crystalline form. During this process, a gas is usually whipped into the solidifying product to adjust the specific gravity of the shortening product, and hence its plasticity. This is done, primarily, to enhance the handling characteristics of the final shortening and to allow it to be better incorporated into a variety of food product systems. The emulsifier may generally be any material suitable for the preparation of shortening, preferably an emulsifier approved as a food additive per 21 C.F.R. § 172, and more preferably is a monoglyceride. The use of the novel soybean oil of the present invention may allow for a reduced level of emulsifier addition to achieve the same functional effects as would be required in a standard soybean oil based shortening arrived at through hydrogenation to attain equal solids.

The soybean seeds, oil, and products therefrom may also find use in a number of additional applications known to the art, including the use in various animal feed applications.

The invention now being generally described, it will be more readily understood by reference to the following examples which are included for purposes of illustration only and are not intended to limit the present invention.

EXAMPLES

Example 1

Plant Expression Vector Construction

Plant vectors are constructed to control the expression of a member of the FatA class of acyl-ACP thioesterases from *Garcinia mangostana* (Garm FatA1, Hawkins and Kridl (1998) supra, and PCT Patent Application WO 96/36719) in seeds of soybean utilizing different seed enhanced promoters.

Figure 1:
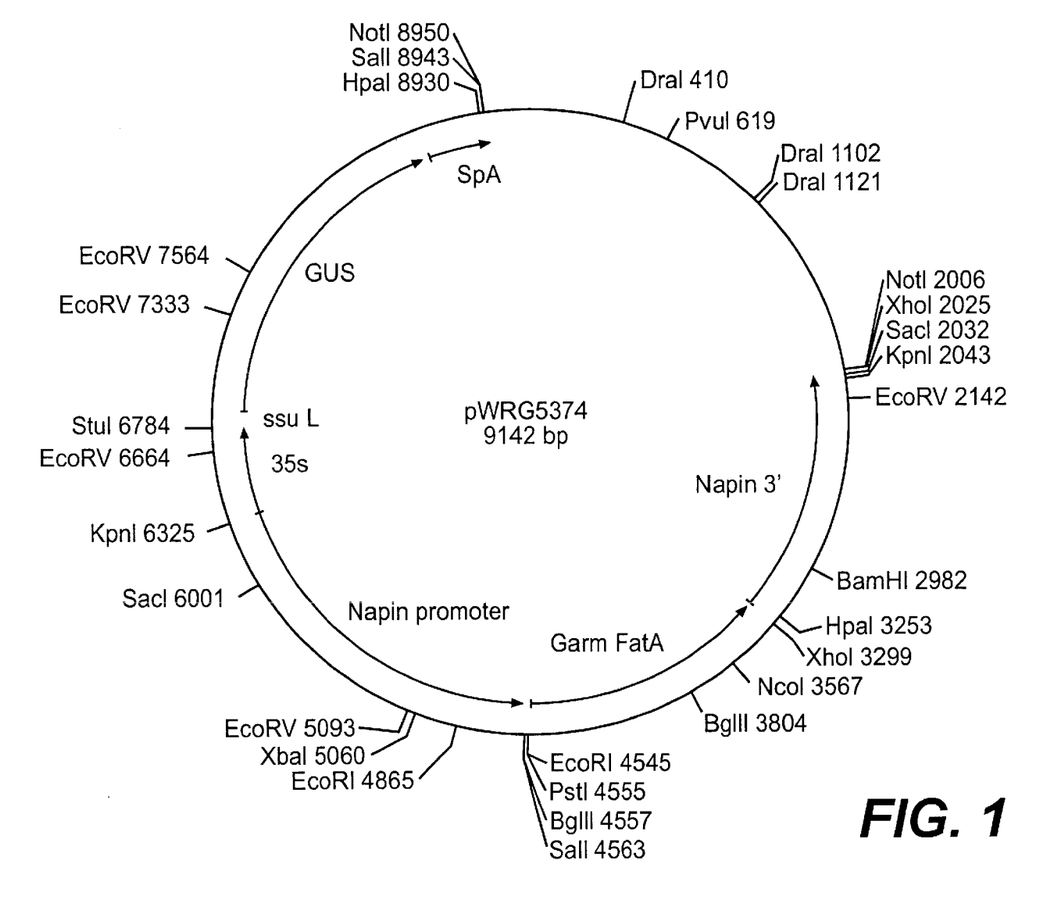
FIG. 1 shows a schematic representation of the binary DNA vector pWRG5374 for plant transformation.

A plant transformation construct, pWRG5374 (FIG. 1), is prepared to express Garm FatA1 in the embryo tissue of the soybean seed utilizing the napin promoter. A DNA fragment containing the napin 5' /Garm FatA1/napin 3', described in Hawkins and Kridl (1998) supra, is cloned into a vector containing the selectable marker β-glucuronidase (GUS, Jefferson et al., *Proc. Natl. Acad. Sci.* (1986) 83:8447–8451) driven by the CAMV 35S (Gardner, et al. (1981) *Nucleic Acids Res.* 9:2871–2888) promoter. The GUS gene contains an untranslated leader sequence derived from a soybean ribulose-bis-phosphate carboxylase (RuBisCo) small subunit, (Grandbastien, et al. (1986) *Plant Mol. Biol.* 7:451–466), ssuL and a translational termination sequence derived from the soybean RuBisCo, (Berry-Lowe (1982) *Jour. Mol. Appl. Genet.* 1:483–498), SpA. Examples of vectors utilizing a GUS selectable marker are described in European Patent 0 301 749 B1, the entirety of which is incorporated herein by reference. The resulting expression construct, pWRG5374, contains the napin 5' /Garm FatA1/ napin 3' sequences as well as the 35S-ssuL/GUS/SpA 3' for transgenic selection by indigo blue staining.

Figure 2:
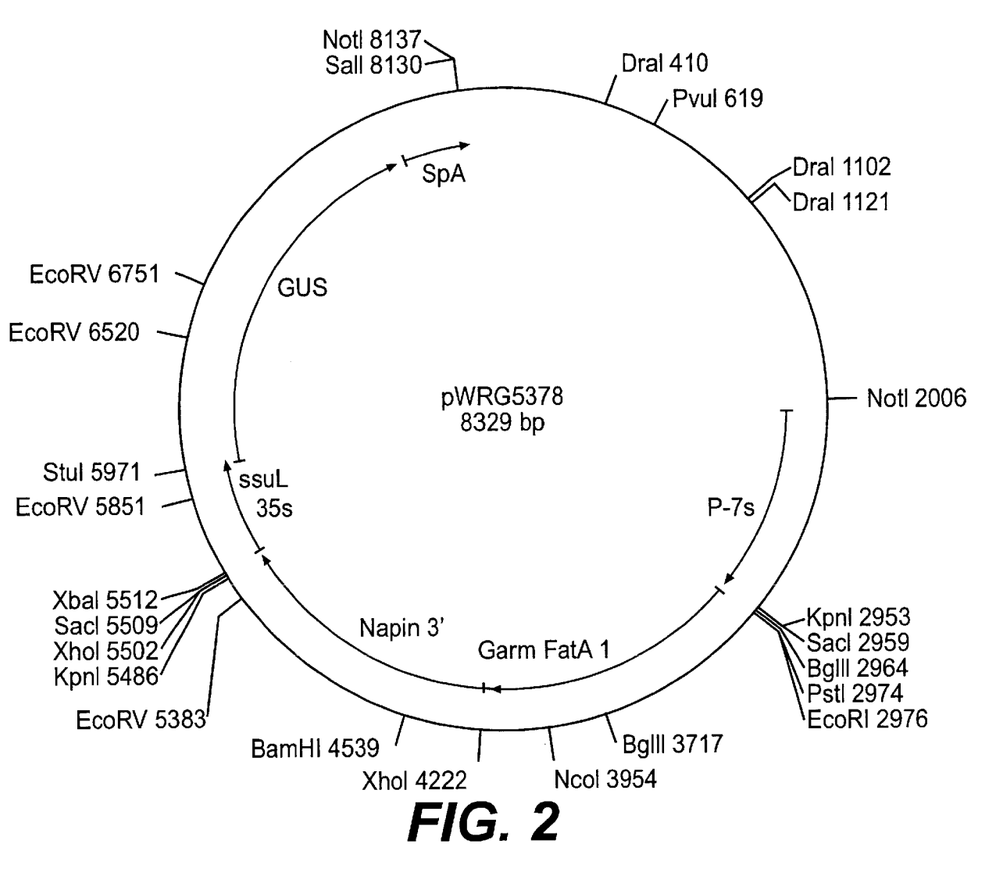
FIG. 2 shows a schematic representation of the binary DNA vector pWRG5378 for plant transformation.
Figure 3A:
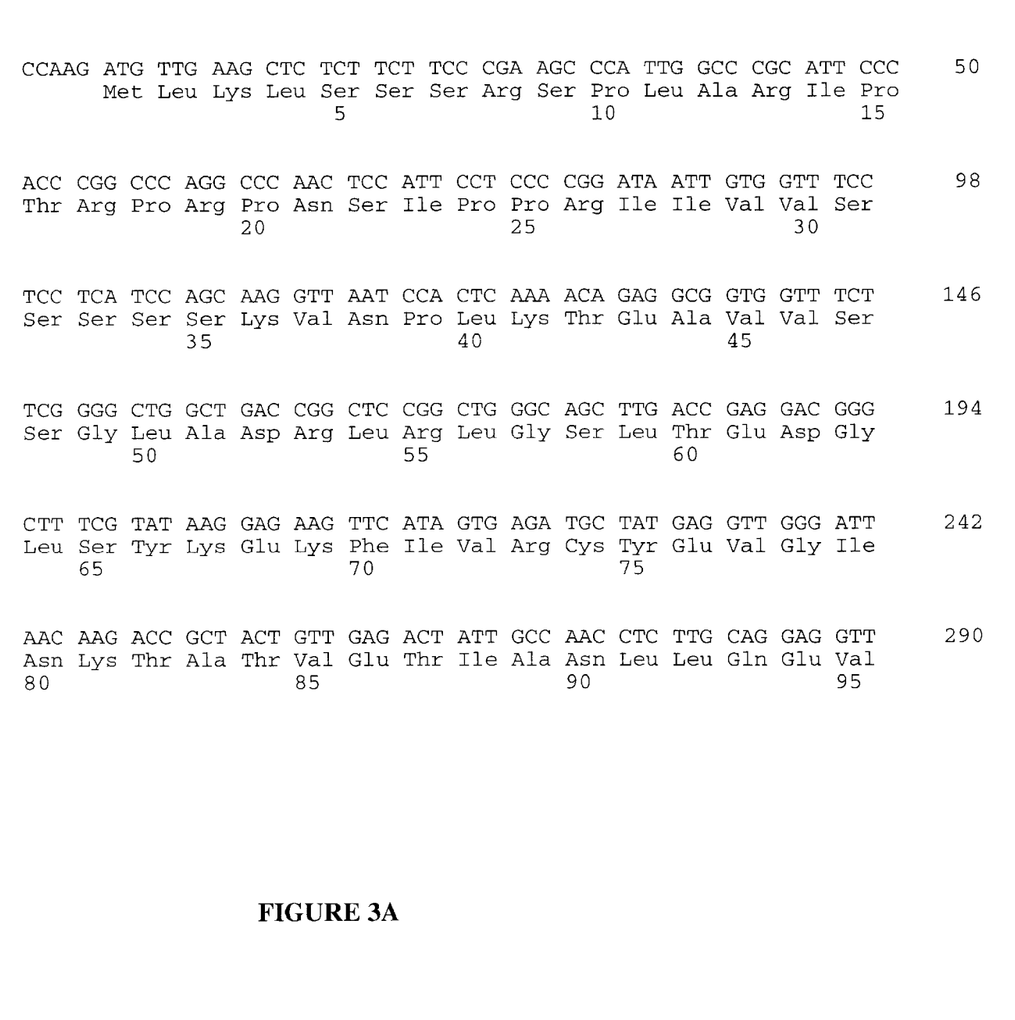
FIGS. 3A–3D Nucleic acid and translated amino acid sequence (SEQ ID NO: 1 and 2) of a mangosteen FatA-type acyl-ACP thioesterase clone (Garm FatA1) is provided. Garm FatA1 demonstrates primary thioesterase activity on 18:1 acyl-ACP substrate, but also demonstrates substantial activity on 18:0 substrate (approximately 10–20% of 18:1 activity), as well as little or no activity on 16:0 substrates.
Figure 3B:
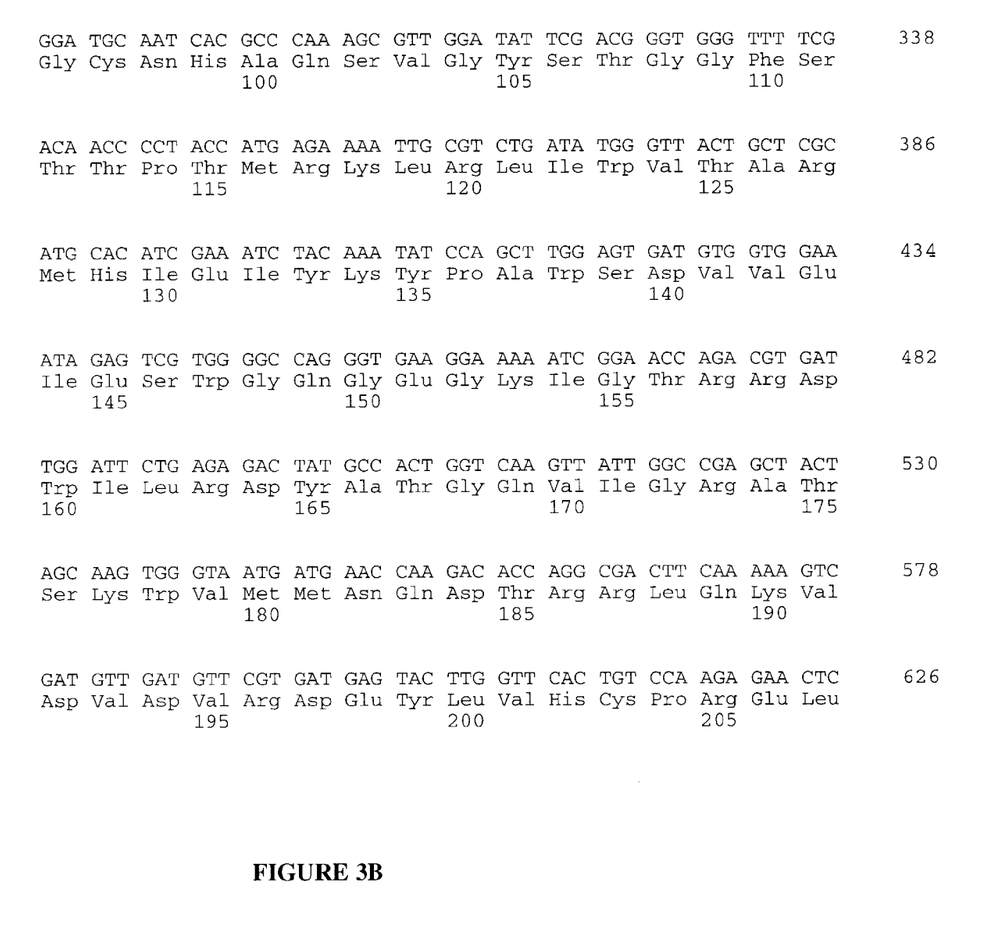
Figure 3C:
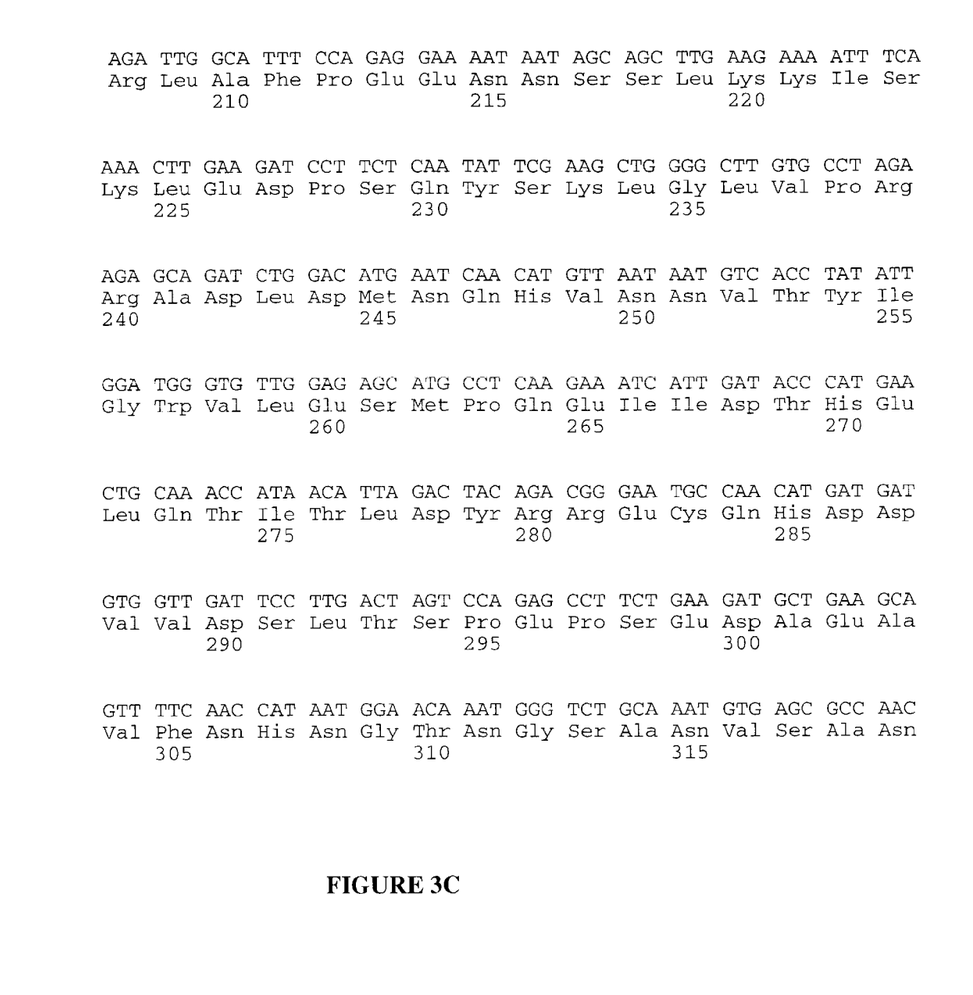
Figure 3D:
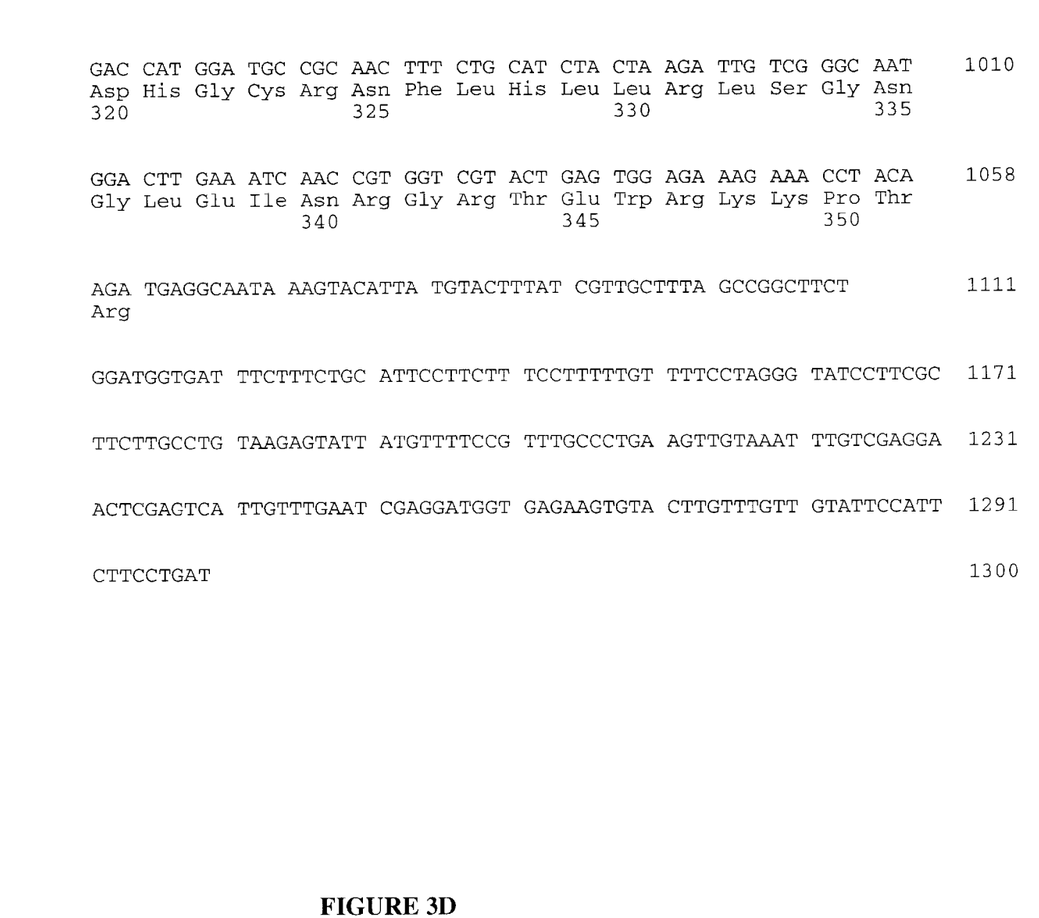

The soybean transformation construct, pWRG5378 (FIG. 2), containing the Garm FatA1 coding sequence expressed from the β-conglycinin 7S subunit promoter was prepared as follows. The Garm FatA1 coding sequence and napin 3' poly-A termination sequences were obtained from plasmid pCGN5253 (described in Hawkins and Kridl (1998) supra). A soybean expression plasmid pWRG5375 was constructed by insertion of the Garm FatA1 coding and napin 3' sequences downstream of a heterologous promoter from the soybean α' subunit of β-conglycinin (soy 7s, (Chen et al., (1986), *Proc. Natl. Acad. Sci.*, 83:8560–8564)). A 941 bp BamHI-XhoI fragment containing the soy 7s promoter was ligated with a 5186 bp fragment from plasmid pCGN5253 produced by partial digestion with KpnI and complete digestion with SalI. Additionally, an 8 bp BamHI-KpnI adapter having the DNA sequence 5'-GATCGTAC-3' was used to fuse the BamHI site from the soy 7s promoter fragment with the KpnI site from pCGN5253. The resulting plasmid was named pWRG5375. A 3477 bp SacII fragment from plasmid pWRG5375 containing the soy 7s/Garm FatA1/napin 3' was ligated to a 6135 bp fragment containing the β-glucuronidase (GUS) marker cassette (described above) for selection of transgenic soybean plants. The soy 7s/Garm FatA1/napin 3' cassette was inserted such that the transcription of the GUS gene was in the same direction as that of the Garm FatA1 coding sequence. The resulting 8329 bp plasmid was designated as pWRG5378.

Example 2

Soybean Transformation with Garm FatA1 Constructs

Plasmids pWRG5374 and pWRG5378 were digested with NotI and linearized fragments containing both the chimeric Garm FatA1 coding sequence and GUS expression cassettes were purified by HPLC. The linear DNA fragments were stably introduced into soybean (Asgrow variety A5403) by the method of McCabe, et.al. (1988) Bio/Technology 6:923–926.

Transformed soybean plants are identified by indigo blue staining of seed tissue with 1 mM X-Gluc (Clontech), 0.1M NaPO$_4$ (pH 7.0), 0.5 mM potassium ferrocyanide.

Example 3

Fatty Acid Compositional Analysis

Fatty acid compositions were analyzed from seed of soybean lines transformed with pWRG5374 or pWRG5378.

One to five seeds of each of the transgenic and control soybean lines were ground individually using a tissue homogenizer (Pro Scientific) for oil extraction. Oil from ground soybean seed was extracted overnight in 1.5 ml heptane containing triheptadecanoin (0.50 mg/ml). Aliquots of 200 gl of the extracted oil was derivatized to methyl esters with the addition of 500 µl sodium methoxide in absolute methanol. The derivatization reaction was allowed to progress for 20 minutes at 50° C. The reaction was stopped by the simultaneous addition of 500 µl 10% (w/v) sodium chloride and 400 µl heptane. The resulting fatty acid methyl esters extracted in hexane were resolved by gas chromatography (GC) on a Hewlett Packard model 6890 GC. The GC was fitted with a Supelcowax 250 column (30 m, 0.25 mm id, 0.25 micron film thickness)(Supelco, Bellefonte, Pa.). Column temperature was 175° C. at injection and the temperature programmed from 175° C. to 245° C. to 175° C. at 40° C./min. Injector and detector temperatures were 250° C. and 270° C., respectively.

The results of the fatty acid compositional analysis from seed oil of the initial transformed 5374 soybean lines is provided in Table 1. Averages are provided where oil compositional analysis was performed on more than one seed from the initial transformant. In seed of transgenic soybean plants expressing Garm FatA1 from the napin promoter, stearate (C18:0) levels were significantly increased over the levels obtained from the seed oil of nontransformed control plants. The increase in stearate is primarily at the expense of oleate, and to a lesser degree linoleate and palmitic all of which were decreased in the transgenic lines. In addition, increases in all saturates examined greater than C18:0 were observed.

TABLE 1

| STRAIN ID | GUS | % 16:0 | % 18:0 | % 18:1 | % 18:2 | % 18:3 | % 20:0 | % 22:0 |
|---|---|---|---|---|---|---|---|---|
| 5374-A5403-3 | + | 6.71 | 24.88 | 14.53 | 43.73 | 6.99 | 1.84 | 1.03 |
| 5374-A5403-3 | + | 6.62 | 26.52 | 11.9 | 44.89 | 7.15 | 1.8 | 0.9 |
| 5374-A5403-3 | + | 7.59 | 22.99 | 13.17 | 45.32 | 8.19 | 1.63 | 0.84 |
| 5374-A5403-3 | + | 7.28 | 23.1 | 13 | 43.65 | 9.74 | 1.88 | 1.13 |
| 5374-A5403-3 | + | 7.39 | 26.54 | 8.4 | 41.95 | 12.38 | 1.9 | 1.07 |
| AVERAGE | | 7.12 | 24.81 | 12.2 | 43.91 | 8.89 | 1.81 | 0.99 |
| 5374-A5403-4 | + | 7.38 | 20.81 | 16.45 | 46.61 | 5.99 | 1.57 | 0.87 |
| 5374-A5403-4 | + | 7.96 | 18.28 | 14.69 | 47.93 | 8.29 | 1.54 | 0.96 |
| 5374-A5403-4 | + | 10.02 | 9.64 | 22.78 | 49.41 | 6.02 | 0.91 | 0.79 |
| 5374-A5403-4 | + | 9.24 | 12.54 | 23.06 | 45.97 | 5.9 | 1.17 | 0.8 |
| 5374-A5403-4 | + | 7.41 | 20.07 | 13.42 | 45.91 | 10.32 | 1.55 | 0.97 |
| AVERAGE | | 8.40 | 16.27 | 18.08 | 47.17 | 7.29 | 1.35 | 0.88 |
| 5374-A5403-14 | + | 7.96 | 38.39 | 7.82 | 37.34 | 6.23 | 2.41 | 1.07 |
| 5374-A5403-35 | + | 9.24 | 33.53 | 11.14 | 38.15 | 7.54 | 1.97 | 0.9 |
| 5374-A5403-36 | + | 8.18 | 19.37 | 13.92 | 47.05 | 8.47 | 1.6 | 1.06 |
| 5374-A5403-36 | + | 7.5 | 19.99 | 13.49 | 47.15 | 8.99 | 1.59 | 0.95 |
| 5374-A5403-36 | + | 7.05 | 23.44 | 10.54 | 46.19 | 9.64 | 1.82 | 0.99 |
| 5374-A5403-36 | + | 7.83 | 20.06 | 13.53 | 47.27 | 8.45 | 1.57 | 0.94 |
| 5374-A5403-36 | + | 7.49 | 22.9 | 11.81 | 46.14 | 8.54 | 1.72 | 1.03 |
| AVERAGE | | 7.61 | 21.15 | 12.66 | 46.76 | 8.82 | 1.66 | 0.99 |
| 5374-A5403-172 | + | 7.92 | 15.53 | 29.9 | 38.2 | 5.8 | 1.36 | 0.89 |
| 5374-A5403-172 | + | 7.37 | 22.45 | 16.63 | 44.3 | 6.58 | 1.56 | 0.77 |
| 5374-A5403-172 | + | 8.74 | 14.38 | 20.17 | 47.33 | 6.94 | 1.17 | 0.84 |
| AVERAGE | | 8.01 | 17.45 | 22.23 | 43.28 | 6.44 | 1.36 | 0.83 |
| Control | | | | | | | | |
| A5403 | − | 11.62 | 4.3 | 24.26 | 49.84 | 7.47 | 0.48 | 0.57 |
| A5403 | − | 12.32 | 4.24 | 21.93 | 52.32 | 7.49 | 0.44 | 0.46 |
| A5403 | − | 12.64 | 4.25 | 20.49 | 53.42 | 7.81 | 0.43 | 0.51 |
| A5403 | − | 12.17 | 4.22 | 21.56 | 52.48 | 8.15 | 0.44 | 0.51 |
| A5403 | − | 11.68 | 4.32 | 25.68 | 49.67 | 7.06 | 0.48 | 0.54 |
| AVERAGE | | 12.09 | 4.27 | 22.78 | 51.55 | 7.60 | 0.45 | 0.52 |

Selected T2 lines also show the trends of increased stearate, and decreased palmitate, oleate and linoleate levels in the seed oil (Table 2). Furthermore, in seed of T2 5374 soybean lines (T3 seed), stearate levels as high as approximately 45% of the fatty acid methyl esters are observed. These levels are increased from approximately 34% in the T1 generation. While null progeny which do not contain the Garm FatA1 transgene contain approximately 4.5% of the fatty acid methyl esters as stearate.

TABLE 2

| STRAIN ID | GUS | 16:0 | 18:0 | 18:1 | 18:2 | 18:3 | 20:0 | 22:0 |
|---|---|---|---|---|---|---|---|---|
| 5374-A5403-3-417 | + | 6.57 | 37.18 | 7.39 | 35.38 | 9.36 | 2.68 | 1.2 |
| 5374-A5403-3-417 | + | 6.52 | 38.66 | 8.26 | 33.82 | 8.43 | 2.78 | 1.29 |
| 5374-A5403-3-417 | + | 6.23 | 39.26 | 7.26 | 35.11 | 7.84 | 2.8 | 1.26 |
| 5374-A5403-3-417 | + | 6.75 | 33.55 | 8.91 | 37.69 | 9.13 | 2.51 | 1.19 |
| 5374-A5403-3-417 | + | 6.18 | 42.21 | 5.88 | 33.36 | 7.99 | 2.94 | 1.23 |
| average | | 6.45 | 38.17 | 7.54 | 35.07 | 8.55 | 2.74 | 1.23 |
| 5374-A5403-35-483 | + | 5.78 | 45.64 | 6.3 | 31.86 | 6.15 | 2.95 | 1.16 |
| 5374-A5403-35-483 | + | 5.82 | 38.21 | 7.83 | 37.06 | 7.22 | 2.54 | 1.12 |
| 5374-A5403-35-483 | + | 5.84 | 38.37 | 7.44 | 37.91 | 6.43 | 2.59 | 1.22 |
| 5374-A5403-35-483 | + | 5.74 | 41.56 | 6.31 | 35.4 | 6.98 | 2.71 | 1.12 |
| 5374-A5403-35-483 | + | 5.58 | 40.35 | 7.06 | 36.91 | 6.11 | 2.63 | 1.16 |
| average | | 5.75 | 40.83 | 6.99 | 35.83 | 6.58 | 2.68 | 1.16 |
| 5374-A5403-172-401 | + | 6.73 | 23.12 | 15.02 | 46.04 | 6.05 | 1.77 | 0.97 |
| 5374-A5403-172-401 | + | 6.92 | 21.96 | 14.85 | 46.47 | 6.7 | 1.78 | 1.02 |
| 5374-A5403-172-401 | + | 6.49 | 24.15 | 14.11 | 45.74 | 6.46 | 1.83 | 0.96 |
| 5374-A5403-172-401 | + | 6.83 | 23.09 | 13.64 | 46.56 | 6.85 | 1.79 | 0.96 |
| 5374-A5403-172-401 | + | 8.32 | 20.32 | 11.94 | 47.05 | 9.36 | 1.69 | 1.02 |
| average | | 7.06 | 22.53 | 13.91 | 46.37 | 7.08 | 1.77 | 0.99 |
| 5374-A5403-36-353 | + | 6.18 | 30.73 | 11.36 | 41.3 | 7.3 | 1.92 | 0.89 |
| 5374-A5403-36-353 | + | 6.42 | 30.82 | 11.14 | 41.03 | 7.53 | 1.85 | 0.85 |
| 5374-A5403-36-353 | + | 6.43 | 30.03 | 11.61 | 40.84 | 8.12 | 1.84 | 0.84 |

TABLE 2-continued

| STRAIN ID | GUS | 16:0 | 18:0 | 18:1 | 18:2 | 18:3 | 20:0 | 22:0 |
|---|---|---|---|---|---|---|---|---|
| 5374-A5403-36-353 | + | 6.66 | 29.27 | 13.98 | 40.82 | 6.26 | 1.77 | 0.83 |
| 5374-A5403-36-353 | + | 6.15 | 30.32 | 13.67 | 40.76 | 5.95 | 1.92 | 0.89 |
| average | | 6.37 | 30.23 | 12.35 | 40.95 | 7.03 | 1.86 | 0.86 |
| 5374-A5403-36-489 | + | 6.57 | 34.87 | 10.56 | 37.1 | 7.23 | 2.34 | 1.09 |
| 5374-A5403-36-489 | + | 6.25 | 37.1 | 8.43 | 37.65 | 7.05 | 2.33 | 1 |
| 5374-A5403-36-489 | + | 6.36 | 36.22 | 10.68 | 36.18 | 6.88 | 2.39 | 1.08 |
| 5374-A5403-36-489 | + | 6.29 | 36.28 | 8.69 | 38.06 | 7.08 | 2.33 | 1.04 |
| 5374-A5403-36-489 | + | 6.26 | 36.6 | 8.33 | 37.79 | 7.25 | 2.44 | 1.11 |
| average | | 6.35 | 36.21 | 9.34 | 37.36 | 7.10 | 2.37 | 1.06 |
| Control | | | | | | | | |
| 5374-A5403-36-341 | − | 10.7 | 6 | 24.46 | 50.9 | 6.29 | 0.53 | 0.61 |
| 5374-A5403-36-341 | − | 11.2 | 4.92 | 20.68 | 54.35 | 7.37 | 0.47 | 0.57 |
| 5374-A5403-36-341 | − | 11.27 | 4.27 | 23.71 | 52.72 | 6.55 | 0.43 | 0.53 |
| 5374-A5403-36-341 | − | 11.33 | 4.78 | 20.4 | 54.38 | 7.58 | 0.46 | 0.55 |
| 5374-A5403-36-341 | − | 11.55 | 4.52 | 18.59 | 55.07 | 8.69 | 0.46 | 0.56 |
| null segregant Ave | | 11.21 | 4.90 | 21.57 | 53.48 | 7.30 | 0.47 | 0.56 |

The results of the fatty acid compositional analysis for transformed 5378 soybean plants are shown in Table 3. Seeds of soybean plants transformed to express Garm FatA1 from the 7S promoter produced increased levels of stearate over those levels observed in seeds of nontransformed control plants. In the seed oil of some T1 5378 transgenic soybean, stearate levels of as high as approximately 53% of the fatty acids were obtained, while levels of approximately 4% were observed in nontransformed control plants.

TABLE 3

| STRAIN ID | GUS | % 16:0 | % 18:0 | % 18:1 | % 18:2 | % 18:3 | % 20:0 | % 22:0 |
|---|---|---|---|---|---|---|---|---|
| 5378-A5403-28 | + | 6.27 | 41.81 | 8.64 | 34.22 | 5.13 | 2.62 | 1 |
| 5378-A5403-28 | + | 6.3 | 42.63 | 10.15 | 32.76 | 4.16 | 2.55 | 0.87 |
| 5378-A5403-28 | + | 6.48 | 43.11 | 7.47 | 33.72 | 5.3 | 2.61 | 1.04 |
| 5378-A5403-28 | + | 6.48 | 43.12 | 9.32 | 32.97 | 4.14 | 2.64 | 1.02 |
| AVERAGE | | 6.38 | 42.67 | 8.90 | 33.42 | 4.68 | 2.61 | 0.98 |
| 5378-A5403-48 | + | 8.19 | 25.51 | 12.37 | 44.21 | 6.85 | 1.62 | 0.88 |
| 5378-A5403-48 | + | 7.74 | 33.77 | 12.13 | 36.33 | 6.41 | 2.23 | 1.05 |
| 5378-A5403-48 | + | 7.42 | 40.06 | 9.82 | 30.97 | 7.26 | 2.84 | 1.23 |
| 5378-A5403-48 | + | 7.89 | 45.26 | 5.73 | 30.23 | 6.8 | 2.71 | 1.06 |
| 5378-A5403-48 | + | 7.04 | 47.2 | 5.69 | 29.58 | 6.13 | 2.86 | 1.2 |
| AVERAGE | | 7.66 | 38.36 | 9.15 | 34.26 | 6.69 | 2.45 | 1.08 |
| 5378-A5403-59 | + | 9.96 | 47.1 | 9.17 | 22.11 | 4.12 | 4.78 | 2.3 |
| 5378-A5403-59 | + | 7.06 | 47.3 | 4.44 | 29.02 | 7.17 | 3.31 | 1.44 |
| 5378-A5403-59 | + | 11.72 | 50.5 | 4.69 | 20.86 | 5.35 | 4.34 | 1.93 |
| 5378-A5403-59 | + | 7.55 | 51.95 | 4.99 | 24.53 | 5.02 | 4 | 1.72 |
| AVERAGE | | 9.07 | 49.21 | 5.82 | 24.13 | 5.42 | 4.11 | 1.85 |
| 5378-A5403-60 | + | 7.7 | 35.2 | 6.09 | 37.85 | 8.77 | 2.74 | 1.34 |
| 5378-A5403-60 | + | 7.19 | 35.53 | 5.86 | 38.36 | 8.57 | 2.79 | 1.41 |
| 5378-A5403-60 | + | 7.27 | 36.4 | 5.51 | 37.78 | 8.61 | 2.78 | 1.35 |
| 5378-A5403-60 | + | 9.01 | 52.21 | 1.71 | 23.14 | 7.62 | 4.41 | 1.59 |
| 5378-A5403-60 | + | 9.83 | 52.94 | 1.77 | 21.85 | 7.59 | 4.28 | 1.42 |
| AVERAGE | | 8.2 | 42.46 | 4.19 | 31.80 | 8.23 | 3.40 | 1.42 |
| 5378-A5403-69 | + | 11.67 | 4.67 | 18.46 | 55.85 | 7.93 | 0.43 | 0.47 |
| 5378-A5403-69 | + | 8.69 | 13.65 | 19.02 | 48.86 | 7.19 | 1.13 | 0.9 |
| 5378-A5403-69 | + | 8.13 | 18.5 | 14.7 | 48.52 | 7.4 | 1.41 | 0.83 |
| 5378-A5403-69 | + | 7.1 | 21.26 | 12.86 | 48.93 | 7.1 | 1.43 | 0.89 |
| 5378-A5403-69 | + | 8.04 | 44.02 | 8.09 | 28.04 | 7.34 | 2.96 | 1.16 |
| AVERAGE | | 8.73 | 20.42 | 14.63 | 46.04 | 7.39 | 1.47 | 0.85 |
| 5378-A5403-103 | + | 9.31 | 40.01 | 8.73 | 30.52 | 7.08 | 2.85 | 1.04 |
| 5378-A5403-103 | + | 7.41 | 49.06 | 4.91 | 28.83 | 5.45 | 2.91 | 1.06 |
| 5378-A5403-103 | + | 11.01 | 49.44 | 4.88 | 22.53 | 7.15 | 3.24 | 1.1 |
| 5378-A5403-103 | + | 7.03 | 49.79 | 4.09 | 29.08 | 5.9 | 2.79 | 1 |
| 5378-A5403-103 | + | 8.32 | 51.04 | 4.29 | 27.06 | 5.1 | 2.91 | 0.92 |
| 5378-A5403-103 | + | 8.52 | 52.59 | 3.69 | 26.35 | 4.64 | 2.93 | 0.86 |
| AVERAGE | | 8.46 | 50.38 | 4.37 | 26.77 | 5.65 | 2.96 | 0.99 |
| Control | | | | | | | | |
| A5403 | − | 11.62 | 4.3 | 24.26 | 49.84 | 7.47 | 0.48 | 0.57 |
| A5403 | − | 12.32 | 4.24 | 21.93 | 52.32 | 7.49 | 0.44 | 0.46 |
| A5403 | − | 12.64 | 4.25 | 20.49 | 53.42 | 7.81 | 0.43 | 0.51 |
| A5403 | − | 12.17 | 4.22 | 21.56 | 52.48 | 8.15 | 0.44 | 0.51 |
| A5403 | − | 11.68 | 4.32 | 25.68 | 49.67 | 7.06 | 0.48 | 0.54 |
| AVERAGE | | 12.09 | 4.27 | 22.78 | 51.55 | 7.60 | 0.45 | 0.52 |

In T3 seed of selected T2 soybean lines, increases in stearate of as high as approximately 53% of the total fatty acid composition were obtained (Table 4), similar to those levels obtained from seed oil from T1 5378 soybean lines. Furthermore, similar to the 5374 soybean plants, decreases in palmitate, oleate and linoleate were observed in both the T2 and T3 seed oil. In addition, increases in saturates greater than C18:0 are also obtained in both the T2 and T3 generations.

TABLE 4

| STRAIN ID | GUS | 16:0 | 18:0 | 18:1 | 18:2 | 18:3 | 20:0 | 22:0 |
|---|---|---|---|---|---|---|---|---|
| 5378-A5403-48-269 | + | 8.63 | 50.62 | 5.5 | 23.07 | 7.4 | 3.34 | 1.14 |
| 5378-A5403-48-269 | + | 8.27 | 53.31 | 4.54 | 23.14 | 6.2 | 3.26 | 1.09 |
| 5378-A5403-48-269 | + | 8.6 | 51.92 | 4.84 | 22.65 | 7.27 | 3.43 | 1.01 |
| 5378-A5403-48-269 | + | 8.62 | 51.62 | 4.39 | 23.2 | 7.43 | 3.46 | 1.06 |
| 5378-A5403-48-269 | + | 9.07 | 50.57 | 4.77 | 22.61 | 7.97 | 3.52 | 1.22 |
| average | | 8.64 | 51.61 | 4.81 | 22.93 | 7.25 | 3.40 | 1.10 |

TABLE 4-continued

| STRAIN ID | GUS | 16:0 | 18:0 | 18:1 | 18:2 | 18:3 | 20:0 | 22:0 |
|---|---|---|---|---|---|---|---|---|
| 5378-A5403-113-304 | + | 6.99 | 49.4 | 4.23 | 29.37 | 6.12 | 2.73 | 0.98 |
| 5378-A5403-113-304 | + | 6.79 | 50.25 | 3.77 | 28.53 | 6.76 | 2.74 | 0.99 |
| 5378-A5403-113-304 | + | 6.79 | 50.19 | 3.73 | 28.8 | 6.61 | 2.75 | 0.98 |
| 5378-A5403-113-304 | + | 6.34 | 47.67 | 4.08 | 30.03 | 7.96 | 2.77 | 1.01 |
| 5378-A5403-113-304 | + | 6.81 | 49.89 | 3.93 | 29.16 | 6.43 | 2.63 | 0.92 |
| average | | 6.74 | 49.48 | 3.95 | 29.18 | 6.78 | 2.72 | 0.98 |
| 5374-36-341 | − | 10.7 | 6 | 24.46 | 50.9 | 6.29 | 0.53 | 0.61 |
| 5374-36-341 | − | 11.2 | 4.92 | 20.68 | 54.35 | 7.37 | 0.47 | 0.57 |
| 5374-36-341 | − | 11.27 | 4.27 | 23.71 | 52.72 | 6.55 | 0.43 | 0.53 |
| 5374-36-341 | − | 11.33 | 4.78 | 20.4 | 54.38 | 7.58 | 0.46 | 0.55 |
| 5374-36-341 | − | 11.55 | 4.52 | 18.59 | 55.07 | 8.69 | 0.46 | 0.56 |
| null segregant Ave | | 11.21 | 4.90 | 21.57 | 53.48 | 7.30 | 0.47 | 0.56 |

The above results demonstrate that by expression of an acyl-ACP thioesterase with substantial activity towards 18:0 acyl-ACP substrates, and capable of producing C18:0 in seed tissue of soybean plants, it is now possible to increase the levels of stearate in the seed oil of soybean.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A soybean seed comprising an introduced nucleic acid sequence having in the 5' to 3' direction of transcription: a promoter that is functional in a soybean seed cell; a DNA sequence encoding Garm FatA1 thioesterase; and a transcriptional termination sequence in which the soybean seed contains about 33 weight percent or greater of stearate, expressed as a component of total fatty acids contained in the soybean seed oil.

2. The soybean seed of claim 1 comprising about 40 weight percent or greater stearate.

3. The soybean seed of claim 2 comprising about 50 weight percent or greater stearate.

4. The seed of claim 1, wherein said DNA sequence comprise SEQ ID NO: 1.

5. The seed of claim 1, wherein said DNA sequence encodes an amino acid sequence comprising SEQ ID NO: 2.

6. The seed of claim 1, wherein said promoter that is functional in a soybean seed cell is selected from the group consisting of an ACP transcriptional initiation control region, a napin transcriptional initiation control region, β-conglycinin 7S transcriptional initiation control region, Lesquerella hydroxylase promoter, and a stearoyl-ACP desaturase promoter.

7. The soybean seed of claim 6 in which the promoter is the β-conglycinin 7S transcriptional initiation control region.

8. The soybean seed of claim 6, in which the promoter comprises the napin transcriptional initiation control region.

9. The soybean seed of claim 1, wherein said promoter that is functional in a soybean seed cell is preferentially expressed in said soybean seed cell.

10. The soybean seed of claim 1, wherein said seed contains up to about 53 weight percent stearate, expressed as a component of the total fatty acids contained in the soybean seed oil.

11. A soybean seed comprising an introduced nucleic acid sequence having in the 5' to 3' direction of transcription: a promoter that is functional in a soybean cell; a DNA sequence encoding Garm FatA1 thioesterase; and a transcriptional termination sequence in which said soybean seed contains between about 33 weight percent and 53 weight percent stearate, expressed as a component of total fatty acids in the soybean seed oil.

12. The seed of claim 11, wherein said DNA sequence comprises SEQ ID NO: 1.

13. The seed of claim 11, wherein said DNA sequence encodes an amino acid sequence that comprises SEQ ID NO: 2.

14. The seed of claim 11, wherein said promoter that is functional in a soybean seed cell is selected from the group consisting of an ACP transcriptional initiation control region, a napin transcriptional initiation control region, β-conglycinin 7S transcriptional initiation control region, Lesquerella hydroxylase promoter, and a stearoyl-ACP desaturase promoter.

15. The soybean seed of claim 14 in which the promoter is the β-conglycinin 7S transcriptional initiation control region.

16. The soybean seed of claim 14 in which the promoter comprises the napin transcription initiation control region.

17. The soybean seed of claim 11, wherein said promoter that is functional in a soybean seed cell is preferentially expressed in said soybean seed cell.

18. The soybean seed of claim 11, wherein said seed contains between about 33 weight percent and 53 weight percent stearate, expressed as a component of the total fatty acids contained in the soybean seed oil.

* * * * *

SEQUENCE LISTING

<160> NUMBER OF SEQ ID NOS: 2

<210> SEQ ID NO 1
<211> LENGTH: 1300
<212> TYPE: DNA
<213> ORGANISM: Garcinia mangostana

<400> SEQUENCE: 1

```
ccaag atg ttg aag ctc tct tct tcc cga agc cca ttg gcc cgc att ccc      50 acc cgg ccc agg ccc aac tcc att cct ccc cgg ata att gtg gtt tcc       98 tcc tca tcc agc aag gtt aat cca ctc aaa aca gag gcg gtg gtt tct      146 tcg ggg ctg gct gac cgg ctc cgg ctg ggc agc ttg acc gag gac ggg      194 ctt tcg tat aag gag aag ttc ata gtg aga tgc tat gag gtt ggg att      242 aac aag acc gct act gtt gag act att gcc aac ctc ttg cag gag gtt      290 gga tgc aat cac gcc caa agc gtt gga tat tcg acg ggt ggg ttt tcg      338 aca acc cct acc atg aga aaa ttg cgt ctg ata tgg gtt act gct cgc      386 atg cac atc gaa atc tac aaa tat cca gct tgg agt gat gtg gtg gaa      434 ata gag tcg tgg ggc cag ggt gaa gga aaa atc gga acc aga cgt gat      482 tgg att ctg aga gac tat gcc act ggt caa gtt att ggc cga gct act      530 agc aag tgg gta atg atg aac caa gac acc agg cga ctt caa aaa gtc      578 gat gtt gat gtt cgt gat gag tac ttg gtt cac tgt cca aga gaa ctc      626 aga ttg gca ttt cca gag gaa aat aat agc agc ttg aag aaa att tca      674 aaa ctt gaa gat cct tct caa tat tcg aag ctg ggg ctt gtg cct aga      722 aga gca gat ctg gac atg aat caa cat gtt aat aat gtc acc tat att      770 gga tgg gtg ttg gag agc atg cct caa gaa atc att gat acc cat gaa      818
```

-continued

```
ctg caa acc ata aca tta gac tac aga cgg gaa tgc caa cat gat gat      866 gtg gtt gat tcc ttg act agt cca gag cct tct gaa gat gct gaa gca      914 gtt ttc aac cat aat gga aca aat ggg tct gca aat gtg agc gcc aac      962 gac cat gga tgc cgc aac ttt ctg cat cta cta aga ttg tcg ggc aat     1010 gga ctt gaa atc aac cgt ggt cgt act gag tgg aga aag aaa cct aca     1058 aga tgaggcaata aagtacatta tgtactttat cgttgcttta gccggcttct          1111
ggatggtgat tcttttctgc attccttctt tccttttgt tttcctaggg tatccttcgc    1171
ttcttgcctg taagagtatt atgttttccg tttgccctga agttgtaaat ttgtcgagga   1231
actcgagtca ttgtttgaat cgaggatggt gagaagtgta cttgtttgtt gtattccatt   1291
cttcctgat                                                           1300
```

<210> SEQ ID NO 2
<211> LENGTH: 352
<212> TYPE: PRT
<213> ORGANISM: Garcinia mangostana

<400> SEQUENCE: 2

```
    Met Leu Lys Leu Ser Ser Arg Ser Pro Leu Ala Arg Ile Pro
    1               5                  10                  15

Thr Arg Pro Arg Pro Asn Ser Ile Pro Pro Arg Ile Ile Val Val Ser
                    20                  25                  30

Ser Ser Ser Ser Lys Val Asn Pro Leu Lys Thr Glu Ala Val Val Ser
                35                  40                  45

Ser Gly Leu Ala Asp Arg Leu Arg Leu Gly Ser Leu Thr Glu Asp Gly
            50                  55                  60

Leu Ser Tyr Lys Glu Lys Phe Ile Val Arg Cys Tyr Glu Val Gly Ile
65                  70                  75

Asn Lys Thr Ala Thr Val Glu Thr Ile Ala Asn Leu Leu Gln Glu Val
80                  85                  90                  95

Gly Cys Asn His Ala Gln Ser Val Gly Tyr Ser Thr Gly Gly Phe Ser
                    100                 105                 110

Thr Thr Pro Thr Met Arg Lys Leu Arg Leu Ile Trp Val Thr Ala Arg
                115                 120                 125

Met His Ile Glu Ile Tyr Lys Tyr Pro Ala Trp Ser Asp Val Val Glu
            130                 135                 140

Ile Glu Ser Trp Gly Gln Gly Glu Gly Lys Ile Gly Thr Arg Arg Asp
    145                 150                 155

Trp Ile Leu Arg Asp Tyr Ala Thr Gly Gln Val Ile Gly Arg Ala Thr
160                 165                 170                 175

Ser Lys Trp Val Met Met Asn Gln Asp Thr Arg Arg Leu Gln Lys Val
                    180                 185                 190

Asp Val Asp Val Arg Asp Glu Tyr Leu Val His Cys Pro Arg Glu Leu
                195                 200                 205

Arg Leu Ala Phe Pro Glu Glu Asn Asn Ser Ser Leu Lys Lys Ile Ser
            210                 215                 220

Lys Leu Glu Asp Pro Ser Gln Tyr Ser Lys Leu Gly Leu Val Pro Arg
225                 230                 235

Arg Ala Asp Leu Asp Met Asn Gln His Val Asn Asn Val Thr Tyr Ile
240                 245                 250                 255

Gly Trp Val Leu Glu Ser Met Pro Gln Glu Ile Ile Asp Thr His Glu
                    260                 265                 270
```

-continued

```
Leu Gln Thr Ile Thr Leu Asp Tyr Arg Arg Glu Cys Gln His Asp Asp
            275                 280                 285

Val Val Asp Ser Leu Thr Ser Pro Glu Pro Ser Glu Asp Ala Glu Ala
            290                 295                 300

Val Phe Asn His Asn Gly Thr Asn Gly Ser Ala Asn Val Ser Ala Asn
    305                 310                 315

Asp His Gly Cys Arg Asn Phe Leu His Leu Leu Arg Leu Ser Gly Asn
320                 325                 330                 335

Gly Leu Glu Ile Asn Arg Gly Arg Thr Glu Trp Arg Lys Lys Pro Thr
                340                 345                 350

Arg
```